(12) United States Patent
Dubois et al.

(10) Patent No.: US 8,785,645 B2
(45) Date of Patent: Jul. 22, 2014

(54) METHOD FOR SYNTHESIZING BIO-BASED PYRIDINE AND PICOLINES

(75) Inventors: Jean-Luc Dubois, Millery (FR); Jean-Francois Devaux, Soucieu En Jarrest (FR)

(73) Assignee: Arkema France, Colombes (FR)

( * ) Notice: Subject to any disclaimer, the term of this patent is extended or adjusted under 35 U.S.C. 154(b) by 172 days.

(21) Appl. No.: 13/505,751

(22) PCT Filed: Oct. 22, 2010

(86) PCT No.: PCT/FR2010/052269
§ 371 (c)(1),
(2), (4) Date: Jul. 20, 2012

(87) PCT Pub. No.: WO2011/055057
PCT Pub. Date: May 12, 2011

(65) Prior Publication Data
US 2012/0283446 A1    Nov. 8, 2012

(30) Foreign Application Priority Data
Nov. 4, 2009  (FR) ...................................... 09 57799

(51) Int. Cl.
*C07D 213/12* (2006.01)
*C07D 213/10* (2006.01)

(52) U.S. Cl.
CPC ............ *C07D 213/12* (2013.01); *C07D 213/10* (2013.01)
USPC ...................................................... 546/251

(58) Field of Classification Search
USPC ............................................................ 546/251
See application file for complete search history.

(56) References Cited

U.S. PATENT DOCUMENTS

| 4,810,794 A | 3/1989 | Shimizu et al. |
| 5,387,720 A | 2/1995 | Neher et al. |
| 5,952,258 A * | 9/1999 | Saitoh et al. .................... 502/61 |
| 6,515,187 B1 | 2/2003 | Schon et al. |
| 2011/0028727 A1 * | 2/2011 | Wenger et al. ................ 546/251 |

FOREIGN PATENT DOCUMENTS

| FR | 2 862 644 A1 | 5/2005 |
| WO | 2008/052993 A2 | 5/2008 |

OTHER PUBLICATIONS

Da Silva, G., et al., "Glycerol: A promising and abundant carbon source for industrial microbiology," Biotechnology Advances, (2009) vol. 27, pp. 30-39, Elsevier Publishing, Barking, GB; Cited in International Search Report issued in corresponding PCT/FR2010/052269 on Jan. 18, 2011.

International Search Report issued in corresponding PCT/FR2010/052269 on Jan. 18, 2011.

* cited by examiner

*Primary Examiner* — Patricia L Morris
(74) *Attorney, Agent, or Firm* — Millen, White, Zelano & Branigan, P.C.

(57) ABSTRACT

The present invention relates to a method for synthesizing bio-based pyridine and picolines, said method including at least the following steps: a first step involving subjecting a glycerol filler, created from the methanolysis of vegetable oils or animal fats, to a dehydration reaction leading to acrolein; a second step involving partial condensation of the effluent from the first step so as to separate a water-rich flow as well as an acrolein-rich flow; and a third step involving reacting the acrolein from the preceding step with acetaldehyde in the presence of ammonia so as to obtain, by means of a condensation reaction, the bio-based pyridine and picolines.

15 Claims, 3 Drawing Sheets

FIG. 1

⊗ Heat exchanger

METHOD FOR SYNTHESIZING BIO-BASED PYRIDINE AND PICOLINES

The present invention relates to a process for synthesizing biosourced pyridine and picolines.

Pyridine, of empirical formula $C_5H_5N$, is an aromatic heterocyclic compound comprising a nitrogen atom; its main derivatives are 2-methylpyridine (or α-picoline), 3-methylpyridine (or β-picoline) and 4-methylpyridine (or γ-picoline). These compounds have been known since the second half of the 19th century. They are either extracted from natural materials such as coal tars, or synthesized chemically especially from aldehydes, ketones or nitriles. Ullmann's Encyclopedia, volume A22, pages 399 to 407 (1993) gives a wide review of the industrial production processes.

The industrial processes generally react ammonia with aldehydes (or ketones) alone or as mixtures. These are short aldehydes (or ketones) generally containing from 2 to 4 carbon atoms; among these aldehydes, α,β-unsaturated compounds such as acrolein are used: see in this respect pages 402 and 403 of the abovementioned encyclopedia. The final product, pyridine or methyl-substituted pyridine, depends essentially on the charge used and on the carbon number of the aldehydes used. The reaction of acetaldehyde, thus involving 3 molecules, with ammonia leads to a substituted pyridine. The reaction of propionaldehyde, thus involving 2 molecules, with ammonia also leads to a substituted pyridine, and this is likewise the case with acrolein. To obtain essentially pyridine, it is necessary to use as charge a mixture of aldehydes in which the sum of the carbon atoms involved is equal to 5, for example acetaldehyde and propionaldehyde, acetaldehyde (2) and formaldehyde, or acetaldehyde and acrolein.

Many industrial processes for synthesizing pyridine and substituted derivatives thereof which are based on these various reactions exist. Among the processes that use acrolein as raw material, mention may be made of the Degussa, ICI, Nippon Kayaku, Koei Chemical and Daicel Chemical processes. The most recent studies relate essentially to the catalytic systems and the operating conditions for increasing the selectivity toward a particular molecule.

In particular, document U.S. Pat. No. 4,810,794 describes a process for producing pyridine bases, i.e. pyridine and picoline derivatives thereof, by reaction of an aliphatic aldehyde and/or a ketone with ammonia in the presence of a catalyst obtained by modification of a zeolite with a high constraint index with at least one metal or an ion of a metal chosen from thallium, lead and cobalt. Said document illustrates the catalytic activity of various zeolites modified solely for the reaction of an acetaldehyde (2)/formaldehyde mixture with ammonia leading mainly to pyridine with the presence of various forms of picoline.

In document U.S. Pat. No. 5,952,258, it is proposed to use as catalyst a zeolite doped with a metal chosen from indium, silver, germanium and gallium for the reaction between acrolein and acetaldehyde in the presence of ammonia, leading to pyridine in a yield of about 45-50%.

The pyridine synthesis processes mentioned above are based on the use of fossil hydrocarbon raw materials, whether they are acetaldehyde or acrolein, whose industrial synthesis is performed by oxidation of propylene and/or propane. These raw materials are derived from petroleum or natural gas, and consequently pyridine is constituted from non-renewable fossil carbon-based raw materials. In addition, the processes for extracting, purifying and synthesizing the raw materials and also the processes for destroying at the end of the cycle the manufactured finished products based on these fossil raw materials generate carbon dioxide, the latter also being a direct by-product of the oxidation reactions of propylene to acrolein. All this contributes towards increasing the concentration of greenhouse gases in the atmosphere. In the context of the undertakings by the majority of the industrialized countries to reduce the emissions of greenhouse gases, it appears particularly important to manufacture novel products based on renewable raw materials that contribute toward reducing these environmental effects.

The need is thus felt for an industrial process for synthesizing "biosourced" pyridine and picoline derivatives thereof. In the rest of the description, the term "pyridine" will denote both pyridine and picoline derivatives thereof. The various picolines are obtained by varying the acetaldehyde/acrolein ratios, but also by means of the impurities, including acetone.

The term "biosourced pyridine" means a compound with a $^{14}C$ carbon content characteristic of the non-fossil natural origin of the raw materials used.

The use of carbon-based raw materials of natural and renewable origin may be detected by means of the carbon atoms included in the composition of the final product. Specifically, unlike materials derived from fossil matter, materials composed of renewable raw materials contain $^{14}C$. All the carbon samples taken from live organisms (animals or plants) are in fact a mixture of three isotopes: $^{12}C$ (representing ~98.892%), $^{13}C$ (~1.108%) and $^{14}C$ (traces: $1.2 \times 10^{-10}$%). The ratio of living tissues is identical to that of the atmosphere. In the environment, $^{14}C$ exists in two predominant forms: in mineral form, i.e. carbon dioxide ($CO_2$) and in organic form, i.e. carbon incorporated into organic molecules.

In a live organism, the $^{14}C/^{12}C$ ratio is kept constant by the metabolism, since the carbon is continuously exchanged with the environment. Since the proportion of $^{14}C$ is substantially constant in the atmosphere, this is likewise the case in the organism, for as long as it is alive, since it absorbs this $^{14}C$ just as it absorbs $^{12}C$. The mean $^{14}C/^{12}C$ ratio is equal to $1.2 \times 10^{-12}$.

$^{12}C$ is stable, i.e. the number of $^{12}C$ atoms in a given sample is constant over time. $^{14}C$ is for its part radioactive and each gram of carbon of a living being contains enough $^{14}C$ isotope to give 13.6 disintegrations per minute.

The half-life (or period) $T_{1/2}$, linked to the disintegration constant of $^{14}C$, is 5730 years. Taking this time into account, it is considered that the $^{14}C$ content is virtually constant from the extraction of the plant raw materials up to the manufacture of the final product.

At the present time, there are at least two different techniques for measuring the $^{14}C$ content of a sample:
  by liquid scintillation spectrometry
  by mass spectrometry: the sample is reduced to graphite or gaseous $CO_2$, and analyzed in a mass spectrometer. This technique uses an accelerator and a mass spectrometer to separate the $^{14}C$ ions from the $^{12}C$ ions and thus to determine the ratio of the two isotopes.

These methods for measuring the $^{14}C$ content of materials are described precisely in standards ASTM D 6866 (especially D 6866-06) and in standards ASTM D 7026 (especially 7026-04). The measuring method preferably used is mass spectrometry described in standard ASTM D6866-06 ("accelerator mass spectroscopy").

One subject of the invention is a process for synthesizing "biosourced" pyridine with a mass content of $^{14}C$ such that the $^{14}C/^{12}C$ ratio is between $0.25 \times 10^{-12}$ and $1.2 \times 10^{-12}$. Preferably, the $^{14}C/^{12}C$ ratio is between $0.5 \times 10^{-12}$ and $1.2 \times 10^{-12}$ and more preferably between $0.9 \times 10^{-12}$ and $1.2 \times 10^{-12}$.

The $^{14}C/^{12}C$ ratio will depend on the manufacturing methods used, the raw materials used, which are totally or partially of non-fossil natural origin, or as a function of mixtures subsequently prepared. This ratio cannot exceed $1.2 \times 10^{-12}$; if such were the case, this would imply that the operator had artificially introduced $^{14}C$ atoms into the pyridine compound.

It should be noted that the literature mentions experiments that are already old, which led to the formation of pyridine and derivatives thereof by reacting ammonia, urea or ammonium salts with glycerol at a temperature at least equal to 300° C. Mention may be made in this respect of Cullinane et al. The *Preparation of Methylpyridines by Catalytic Methods*, pages 142-143; J.S.C.I., 67, April, 1948; and J. Gelas and R. Rambaud *Décomposition du glycérol en présence de sels d'ammonium [Decomposition of glycerol in the presence of ammonium salts]*, pages 2386 to 2392, Bulletin de la Société Chimique de France 1970, No. 6. The yields of pyridine, as a mixture with many other compounds, are in the best of cases about 10% and in no way capable of passing to the industrial scale.

The aim of the invention is thus to overcome the preceding drawbacks by proposing a process for synthesizing "biosourced" pyridine using non-fossil natural raw materials.

The process for synthesizing pyridine and picolines according to the invention comprises at least the following steps:
- a first step consisting in subjecting a glycerol charge derived from the methanolysis of plant oils or animal fats to a dehydration reaction leading to acrolein according to the reaction $CH_2OH\text{---}CHOH\text{---}CH_2OH \rightarrow CH_2\text{=}CH\text{---}CHO + 2H_2O$ and then
- a second step that consists in performing a partial condensation of the effluent derived from the first step, to separate on the one hand a stream rich in water and, on the other hand, a stream rich in acrolein,
- a third step which consists in reacting the acrolein obtained from the preceding step with acetaldehyde, in the presence of ammonia, to obtain, via a condensation reaction, biosourced pyridine and picolines.

The charge used in the 1st step of the first process is glycerol—1,2,3-propanetriol—which is a coproduct formed during the methanolysis or more generally alcoholyses, hydrolyses and saponifications, of plant oils or animal fats, the other coproduct being the methyl esters, which are used especially as diesel and domestic fuel, or fatty acids (hydrolysis) or soaps (saponification). The development of biofuels entails an increase in glycerol production according to this pathway in which glycerol represents about 10% of the weight of the transformed oil.

Glycerol may be subjected beforehand to various purification treatments aimed at removing the salts by distillation, by using ion-exchange resins, or by using a fluidized bed (French patent application 2 913 974) or the purification and evaporation of glycerol, which are described especially by G. B. D'Souza in J. Am. Oil Chemists' Soc. November 1979 (Vol 56) 812A, by Steinberner U et al. in Fat. Sci. Technol. (1987), 89 volume No. 8, pp. 297-303 and by Anderson D. D. et al. in Soaps and Detergents: A theoretical and Practical Review, Miami Beach Fla., Oct. 12-14 1994, chapter 6, pp. 172-206. Ed: L Spitz, AOCS Press, Champaign.

Aqueous solutions of glycerol whose concentration may vary within a wide range, for example from 20% to 99% by weight of glycerol, are generally used, and solutions comprising from 30% to 80% by weight of glycerol are preferably used.

The dehydration reaction:

is an equilibrated reaction which is favored by a high temperature level. It is generally performed in the gas phase in the reactor in the presence of a catalyst, at a temperature ranging from 150° C. to 500° C., preferably between 250° C. and 350° C., and a pressure of between 1 and 5 bar. It may also be performed in the liquid phase. It may also be performed in the presence of oxygen or of a gas containing oxygen as described in patent applications WO 06/087 083 and WO 06/114 506. In these processes, the oxygen does not serve for oxidation, but in fact contributes towards decoking the catalyst (by burning the coke), which is not oxidant (in the sense that little acrylic acid and acetic acid are formed), but acidic, which catalyst rapidly becomes fouled, and thus towards prolonging its service life; in addition, it also contributes towards reducing the formation of interfering by-products such as phenol, acetone and propionaldehyde, for example. As long as the temperature is not too high, there is no oxidation to acrylic acid.

The dehydration reaction of glycerol is generally performed on solid acid catalysts. The catalysts that are suitable for use are homogeneous or multiphase materials, which are insoluble in the reaction medium and which have a Hammett acidity, noted $H_0$, of less than +2.

As indicated in U.S. Pat. No. 5,387,720, which makes reference to the article by K. Tanabe et al. in "Studies in Surface Science and Catalysis", volume 51, 1989, chapters 1 and 2, the Hammett acidity is determined by amine titration using indicators or by adsorption of a base in the gaseous phase.

These catalysts may be chosen from natural or synthetic siliceous materials or acidic zeolites; mineral supports, such as oxides, covered with mono-, di-, tri- or polyacidic inorganic acids; oxides or mixed oxides, or alternatively heteropolyacids or salts of heteropolyacids.

These catalysts may generally consist of a heteropolyacid salt in which protons of said heteropolyacid are exchanged with at least one cation chosen from elements belonging to groups I to XVI of the Periodic Table of the Elements, these heteropolyacid salts containing at least one element chosen from the group comprising W, Mo and V.

Among the mixed oxides, mention may be made particularly of those based on iron and phosphorus, those based on vanadium and phosphorus, those based on aluminum and phosphorus, boron and phosphorus, phosphorus or silicon and tungsten and those based on cesium, phosphorus and tungsten.

The catalysts are especially chosen from zeolites, Nafion® composites (based on sulfonic acid of fluoropolymers), chlorinated aluminas, acids and salts of phosphotungstic and/or silicotungstic acids, and various solids of metal oxide type such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2$—$Al_2O_3$, impregnated with acidic functions such as borate $BO_3$, sulfate $SO_4$, tungstate $WO_3$, phosphate $PO_4$, silicate $SiO_2$ or molybdate $MoO_3$, or a mixture of these compounds.

The preceding catalysts may also comprise a promoter such as Au, Ag, Cu, Pt, Rh, Pd, Ru, Sm, Ce, Yt, Sc, La, Zn, Mg, Fe, Co, Ni.

The preferred catalysts are phosphate-containing zirconias, tungsten-containing zirconias, siliceous zirconias, titanium oxides or tin oxides impregnated with tungstate, silicotungstate or phosphotungstate, phosphate-containing aluminas or silicas, heteropolyacids or heteropolyacid salts, iron phosphates and iron phosphates comprising a promoter, vanadium-phosphorus mixed oxides, and also combinations of these various catalysts, or catalysts consisting of a support and an active phase comprising one of the abovementioned catalysts. The supports that may be suitable for use comprise, for example, alumina, silica, titanium oxide, zirconium oxide and niobium and tantalum oxides.

The second step is performed in a condensation unit consisting of an absorption column, a heat exchanger, a condenser or any equivalent system. The gaseous effluent obtained from the dehydration reactor is subjected, at the outlet thereof, to cooling of "quench" type in a "gas boiler-heat exchanger" with production of steam, and then sent to the condensation unit operating at a temperature generally of between 0 and 90° C., the temperature of the gases at the top of the column preferably being between 30 and 60° C. and that of the liquid at the bottom of the column being between 60 and 90° C. In this column, the heavy compounds, acrylic acid, acetic acid and also glycerol polyethers, glycerol acetals, residual glycerol, etc., are separated out by withdrawing an aqueous solution at the bottom, whereas the gaseous fraction containing acrolein, acetaldehyde, propionaldehyde, acetone and the unreacted gases $O_2$ and $N_2$, and also the uncondensable gases CO and $CO_2$ is given off at the top. The gaseous fraction from this first column is then subjected to a purification to obtain the desired quality of acrolein, with or without separation of the acetaldehyde, which may be subjected to the third step of the process according to the invention.

According to one embodiment of the invention, the gaseous fraction from this first column is sent to a second absorption column, at the bottom of which is collected an aqueous acrolein solution, the uncondensable compounds being purged at the top of the column. It then suffices to distill the aqueous acrolein solution also containing propionaldehyde and acetone, to obtain the desired quality of acrolein, with or without separation of the acetaldehyde depending on the need.

Certain distillation columns may be grouped together in order to limit the investment costs, as illustrated in the schemes featured in Techniques de l'Ingénieur J-6100, page 2 and in Ullmann's Encyclopedia volume A1, page 154 and Kirk-Othmer's Encyclopedia, third Edition, volume 1, page 287, for example. In particular, the separation of acrolein, acetaldehyde and water may be grouped together in a single column as described in U.S. Pat. No. 6,515,187.

The aqueous fraction collected at the bottom of the absorption column, which is rich in acrolein containing the light by-products such as acetaldehyde, propionaldehyde and acetone is sent to the third step after optional purification treatments.

According to one embodiment of the invention, the aqueous acrolein solution is sent to a distillation column where an acrolein-rich fraction containing acetaldehyde is separated out at the top and an aqueous solution is separated out at the bottom and is recycled into the second absorption column.

According to one embodiment of the invention, the aqueous acrolein solution is sent to a first distillation column where a light fraction enriched in acetaldehyde is separated out at the top and an aqueous acrolein solution is separated out at the bottom and is sent into a second distillation column where a fraction enriched in acrolein is separated out at the top and an aqueous solution is separated out at the bottom and is recycled into the second absorption column.

According to one embodiment of the invention, the aqueous acrolein solution is sent to a distillation column where a light fraction containing acetaldehyde is separated out at the top, and a fraction enriched in acrolein is withdrawn laterally in an intermediate zone, and an aqueous solution is separated out at the bottom and is recycled into the second absorption column.

During the third step of the process according to the invention, the acrolein obtained in the preceding step is reacted with acetaldehyde in the presence of ammonia to obtain, via a condensation reaction, biosourced pyridine and picolines.

This reaction, the reaction scheme of which is described below, is performed in the gaseous phase at a temperature of between 300 and 600° C. and preferably between 350 and 550° C., at an hourly space velocity (HSV) of 500 to 5000 $h^{-1}$, at a pressure generally of between 0.5 and 10 bar, preferably between 0.8 and 2 bar, in the presence of a solid acid catalyst consisting of a silica-alumina preferably having an Si/Al atomic ratio of greater than 10, where appropriate comprising a promoter. Examples of such catalysts that may also be mentioned include crystalline or amorphous aluminosilicates, silicalites, crystalline synthetic zeolites such as faujasite, ferrierite, ZSM-5, in forms thereof which are acidic or partially or totally neutralized with elements from groups 1 to 14 and preferably from groups 1 and 2 and with Zn and Tl, mixed oxide catalysts of the type such as mixed phosphates of cobalt and aluminum, alumina or silica-alumina doped, for example, with halides of cadmium, Mg, Ca, Sr, Mn, Zn, Mo, Nb, Pb, Si, etc. The zeolites used may have in their structure some or all of the aluminum atoms replaced with trivalent atoms such as B, Ga, Fe, Cr, V, As, Sb, Bi or Be, and may have some or all of the silicon atoms replaced with tetravalent atoms such as Ge, Ti, Zr or Hf.

The catalysts that may be used in the process of the invention are well known to those skilled in the art; these catalysts have been the subject of recent studies in this field to obtain better selectivity. Mention may be made of U.S. Pat. Nos. 4,810,794; 4,868,179; 5,079,367; 5,395,940; and 5,952,258. The choice of catalyst makes it possible more or less to orient the selectivity toward pyridine or its derivatives β-picoline, or α-picoline and γ-picoline. The most important factor for orienting the selectivity toward a particular molecule lies in the nature and respective amounts of reagents used. When the target molecule is pyridine, acetaldehyde is added to the reaction medium in an amount such that the acrolein/acetaldehyde mole ratio is between 0.8 and 1.2 and preferably between 0.9 and 1.1, the stoichiometric amount being 1, and ammonia in an amount such that the ammonia/acrolein+acetaldehyde mole ratio is between 2 and 20.

The reaction is preferably performed in the presence of oxygen or air, which will make it possible to avoid rapid deactivation of the catalyst, which may, however, be regenerated by treatment in air at 550° C.

In another preferred embodiment of the invention, the reaction is performed in the presence of hydrogen, which will make it possible to avoid rapid deactivation of the catalyst. The hydrogen used may be derived from a recycling of the reaction gases or may be added continuously into the process.

The reaction scheme is as follows:

Under the synthetic conditions, other reactions may take place depending on the molecules (impurities) present in the medium.

The composition of the mixture entering the pyridine synthesis reactor determines in part the mole ratios in which the various products—pyridine and picolines—are obtained. Numerous variations described in the prior art exist.

At the outlet of the condensation reactor, the gaseous effluent containing pyridine is cooled. The gaseous fraction, essentially ammonia, is extracted at the top for purification and recycling. The liquid fraction is subjected to a solvent extraction, generally with benzene. The solvent-containing solution is then subjected to a fractional distillation to extract at the top the solvent that is recycled into the preceding phase. The pyridine-rich heavy fraction, generally referred to as pyridine base, is subjected to a series of distillations to separate the various forms of pyridine.

The pyridine obtained according to this process has a $^{14}C/^{12}C$ ratio at least equal to $0.7 \times 10^{-12}$.

This embodiment of the process of the invention has, relative to a process using acrolein derived from propylene, the great advantage of consuming less acetaldehyde. Specifically, acrolein produced by oxidation of propylene generally contains less than 0.1% by mass of propionaldehyde and less than 2% by mass of acetaldehyde. During the glycerol dehydration step, the main by-product of the dehydration process is acetaldehyde, which is often present in a proportion of from 2% to 10% by mass, the propionaldehyde being present in a proportion of from 0.5% to 5% by mass. The gaseous stream leaving the first step of the process according to the invention consequently already comprises two of the reagents—acrolein and acetaldehyde—involved during the third step of the process according to the invention, where it will suffice to adjust the proportions by addition of acetaldehyde.

Furthermore, propionaldehyde, which is an impurity that is difficult to separate out, can be upgraded in the medium by reaction with acrolein to form β-picoline. Consequently, the by-products present in the acrolein derived from an ex-glycerol process contribute toward improving the yield of the process for synthesizing pyridine bases.

In another embodiment of the process of the invention, a biosourced acetaldehyde obtained from bioethanol will be used as reagent for the third step.

This transformation may be obtained according to two slightly different reaction modes. The first consists of an oxidation according to the following reaction:

$$2CH_3\text{---}CH_2OH+O_2 \rightarrow 2CH_3\text{---}CHO+2H_2O.$$

This reaction is performed in the gaseous phase at a temperature of between 200 and 500° C. under a pressure of between 1 and 5 bar absolute, generally at a substantially atmospheric pressure, and in the presence of a solid catalyst chosen from iron molybdate, iron tungstate, and mixed oxides of molybdenum and of at least one metal W, V, Cu, Nb or Ti.

In the other reaction mode, acetaldehyde is obtained by oxydehydrogenation of ethanol according to the following reaction:

$$CH_3\text{---}CH_2OH \rightarrow CH_3\text{---}CHO+H_2$$

This reaction is performed in the gaseous phase at a temperature of between 500 and 700° C. in the presence of a silver or copper metal catalyst under a substantially atmospheric pressure.

It is possible to synthesize acetaldehyde according to a process combining the two reaction modes according to the combination of the following reactions:

$$2CH_3\text{---}CH_2OH+O_2 \rightarrow 2CH_3\text{---}CHO+2H_2O$$

$$CH_3\text{---}CH_2OH \rightarrow CH_2\text{---}CHO+H_2$$

$$2H_2+O_2 \rightarrow 2H_2O$$

This combination of reactions is performed in the gaseous phase at a temperature of between 400 and 700° C. under a pressure of between 1 and 5 bar absolute and in the presence of a solid catalyst chosen from copper metal, silver metal, silver metal supported on various supports including silicon carbide, silica, alumina and titanium oxide.

These various reactions are described in Ullmann's Encyclopedia volume A1, pages 34-35 and also in the publication from the Institut Français du Pétrole *Procédés de pétrochimie* volume 2, 1986 edition, pages 33 to 36.

The other steps are strictly identical to those of the process described previously.

The pyridine obtained according to this process has a $^{14}C/^{12}C$ ratio at least equal to $1.1 \times 10^{-12}$.

BRIEF DESCRIPTION OF THE DRAWINGS

The process of the invention will be understood more clearly in the light of the description given below with reference to the attached figures.

Figure 1:
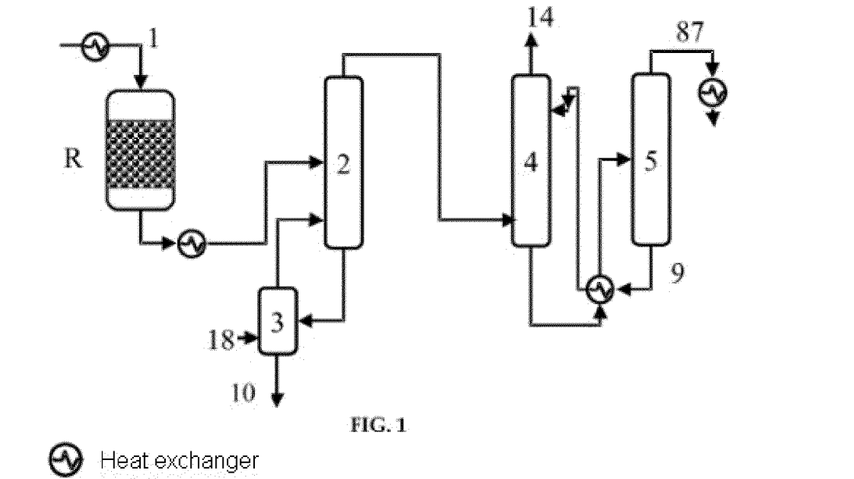
FIG. 1 illustrates steps 1 and 2 of the process targeting the synthesis of acrolein followed by the purification steps by removal of the heavy and uncondensable compounds.

According to FIG. 1, the glycerol charge in aqueous solution is introduced into the reactor R containing the acid catalyst, via line 1, after preheating, along with oxygen and an inert gas, such as nitrogen. During the operation, all or part of the nitrogen may be replaced with the uncondensable gases extracted from column 4 via line 14. The reactor is maintained at a temperature of between 250 and 350° C. and under a pressure of 1 to 5 bar. At the reactor outlet, the gaseous effluent is cooled upstream of the condensation column 2. In column 2, the heavy fraction is withdrawn at the bottom and is sent to a column 3 where it is subjected to stripping, the aim of which is to recover the light aldehydes that have been entrained in the heavy stream containing the acidic and heavy compounds. This stripping of the lightest compounds may optionally be facilitated by using a stripping gas, introduced via line 18, which may be air, diluted air or recycling gases, for instance those obtained at the top of column 4. Air ($O_2$) may also inhibit polymerization reactions in the columns provided that a limited amount thereof is used such that it does not entail flammable conditions. The heavy fraction is removed via stream 10. The light fraction is extracted at the top of the column and recycled into the bottom of column 2. The light fraction from column 2 is taken out at the top of the column and sent to a column 4 for removal of the uncondensable gases by stripping following the absorption of the light aldehydes into the aqueous solution. In this column 4, the uncondensable compounds are extracted at the top of the column via line 14 and the liquid effluent withdrawn at the bottom of the column is sent, after heating by heat exchange, to a column 5 where the light fractions are separated out via line 87, into a stream combining acrolein, acetaldehyde and the other light aldehydes and ketones, and the water-rich tail effluent is recycled via line 9 into column 4. This stream 87 may be used as charge for a reactor for pyridine synthesis by condensation, such as the one referenced as 15 in FIGS. 4 and 5, with ammonia and additional acetaldehyde.

Figure 2:
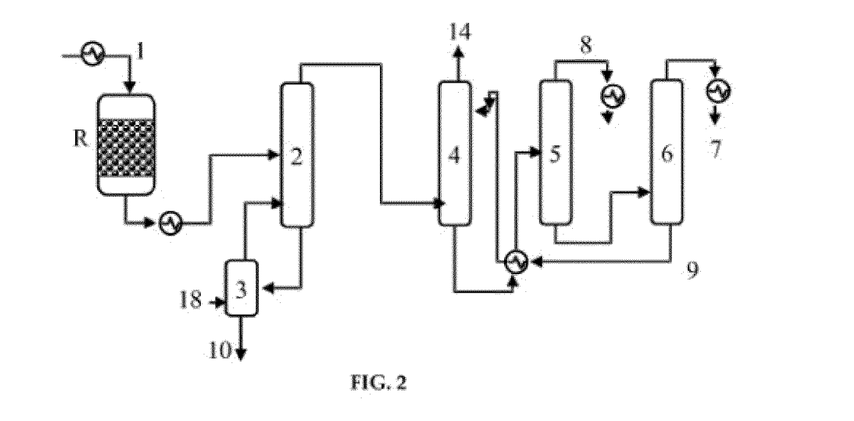
FIG. 2 illustrates steps 1 and 2 of the process as in FIG. 1, but with separate extraction of the acetaldehyde and the acrolein.

The scheme of FIG. 2 is similar to that of FIG. 1, except that a column 6 is added and powered with the effluent in the bottom of column 5. At the top of column 5, a stream rich in acetaldehyde (and light fractions) is extracted via line 8 and at the bottom of this column, an aqueous stream enriched in acrolein is withdrawn and is sent in column 6. At the top of column 6, the acrolein-rich gaseous stream is extracted at the top via line 7 and the water-rich tail effluent is recycled via line 9 into column 4.

Figure 3:
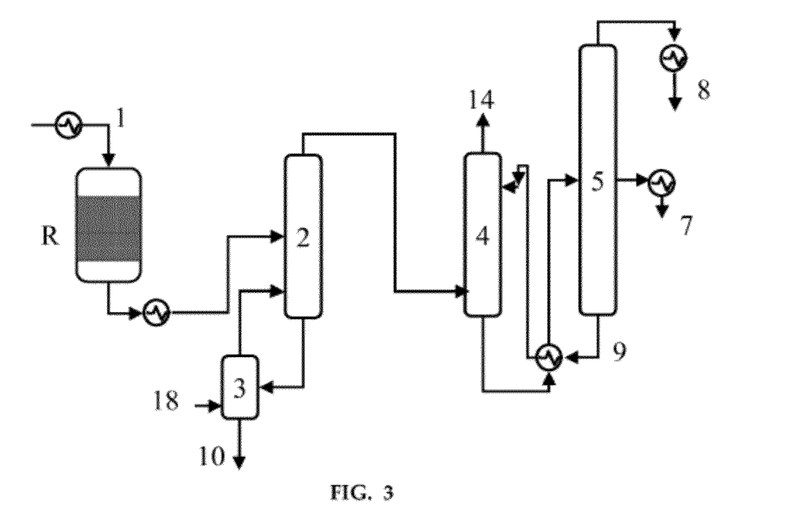
FIG. 3 illustrates steps 1 and 2 of the process with separate extraction of the acetaldehyde and the acrolein in the same column.

The scheme of FIG. 3 is similar to that of FIG. 1 except that column 5 is modified and equipped with lateral withdrawal for simultaneously extracting via line 7, located at an intermediate level, the acrolein-rich gaseous stream and, at the top, acetaldehyde and the light fractions via line 8.

It should be noted that certain separations by distillation may necessitate raising of the temperature; in this case, a reboiler may be inserted at the bottom of the column. To simplify the presentation, this reboiler is not systematically indicated in the schemes.

Figure 4:
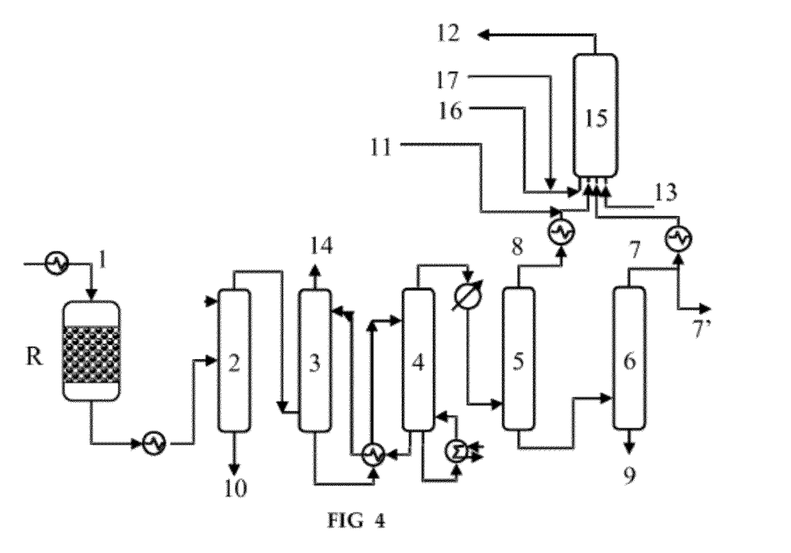
FIG. 4 illustrates the scheme of a complete process with its three steps.

FIG. 4 represents the scheme of the assembly for a process with its three steps. It is identical to the scheme of FIG. 2 for all the upstream part of the process, from the reactor R to column 6 with, however, two differences, column 4 is equipped with a reboiler for raising its temperature and the water-rich effluent is extracted purely and simply via line 9. Downstream of columns 5 and 6, the streams 7 and 8, which have been heated, are sent to reactor 15 to perform the synthesis of pyridine (and picolines) by condensation with ammonia introduced via line 13. Via a line 11, additional acetaldehyde is introduced. Air (or a source of oxygen) is introduced into reactor 15 via line 16, along with nitrogen via line 17. This reactor, operating in the gas phase at a temperature generally of between 350 550° C., at a pressure generally of between 0.8 and 2 bar and an HSV ranging from 500 to 5000 $h^{-1}$, is equipped with the solid acid catalyst for the condensation reaction. The gaseous effluent containing pyridine and its derivatives is extracted via line 12. Since the reaction needs to be performed with substantially equimolar amounts of acrolein and acetaldehyde, in the case where the desired product is mainly pyridine, the amount of acetaldehyde required for the reaction that is not supplied via line 8 is supplemented by an additional amount via the channel of line 11.

In an implementation variant of the process described in FIG. 4, an autonomous unit for producing pyridine (and derivatives) and acrolein may be made to function without external supply of acetaldehyde. Specifically, the acrolein-rich effluent derived from column 6 and taken out via line 7 may be separated into two streams: stream 7' serving for the manufacture of acrolein as product, and the remainder being the reagent sent to reactor 15. It suffices to choose the withdrawal output 7' in order for its supplement to correspond to an amount of acrolein substantially equal to that of the acetaldehyde contained in the stream 8 that needs to enter the reaction in reactor 15, i.e. such that the acrolein (7)/acetaldehyde (8) mole ratio is between 0.8 and 1.2, this being done while dispensing with the additional feed via line 11.

In this configuration of the process scheme, it is not necessary for the separation in column 5 of the acrolein and acetaldehyde to be perfect. Column 5 may be regulated such that it lets pass into the stream 8 all of the acetaldehyde and, as a result, also a certain amount of acrolein at the top with other light aldehydes and ketones. The reason for this is that it is preferable to leave acrolein in the acetaldehyde, and to send for separation in column 6 a stream that is poorer in acetaldehyde, but which at the same time has a lower output, without needing to excessively enlarge column 5, which makes it possible to reduce the necessary investment costs and to satisfy more easily the acrolein quality criteria.

Figure 5:
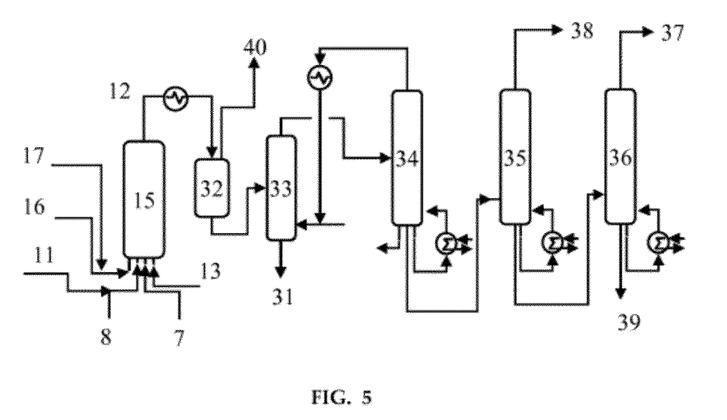
FIG. 5 illustrates the process for synthesizing pyridine from acrolein and acetaldehyde.

In this configuration by combination of a production of acrolein and pyridine, the streams are better upgraded, which consequently facilitates the industrial application. Formaldehyde, acetaldehyde, acetone, propionaldehyde and acrolein, i.e. all the light aldehydes and ketones present in column 5, can be left in stream 8. FIG. 5 illustrates the phase of the process targeting the synthesis of pyridine (and derivatives) via a condensation reaction between ammonia, acrolein and acetaldehyde and also the train of purifications of the reaction products. This reaction is performed under the conditions described above with reference to FIG. 4. The various reagents and components of the medium are introduced via lies 7 (acrolein), 8 and 11 (acetaldehyde), 13 (ammonia), 16 (oxygen) and 17 (nitrogen). The reaction effluent is extracted via line 12 and sent after cooling to a collector 32, where the hydrogen formed and the excess ammonia are extracted via line 40. This excess ammonia is sent to a purification phase in order to be reused in the process. The liquid effluent withdrawn from the collector 32 is sent to an extractor 33, where an extraction with benzene is performed. The residual aqueous fraction is withdrawn at the bottom via line 31. The benzene solution extracted at the top is sent to a column 34, where the solvent leaving at the top of the column is distilled off and is recycled after cooling into the extractor 33. The effluent from the bottom of the column consisting of a mixture of pyridine and its various derivatives is sent into a first distillation column 35, where the lightest compounds, pyridine and 2-methylpyridine are separated out at the top, and the heavy fraction is sent to a second distillation column 36, where 3-methylpyridine and 4-methylpyridine are separated out at the top and the compounds of heavy pyridine type, the high-boiling pyridine bases, are withdrawn at the bottom via line 39.

In another embodiment, it may be envisioned to increase the number of distillation columns in order to obtain pyridine and its various derivatives in pure form. Specifically, their boiling points are as follows: pyridine: 113.5-115.5° C.; 2-methylpyridine: 128-129° C.; 3-methylpyridine and 4-methylpyridine: 143-146° C.

EXAMPLES

The percentages used in the examples are mass percentages.

Example 1

0.100 mol/h of acrolein produced from glycerol (composed of 89% acrolein, 7% acetaldehyde, 1% propionaldehyde and 3% water), 0.0500 mol/h of acetaldehyde (99.5% pure) and 0.200 mol/h of ammonia are introduced into a vaporizer. The gaseous stream is sent over 16 ml of an HZSM-5/In catalyst obtained according to the process described in document U.S. Pat. No. 595,228, with a mean particle size of 0.5 mm, placed in a tube raised to 450° C.

The gaseous stream leaving the reactor is absorbed in water and analyzed by gas chromatography to determine the reaction yields.

0.0420 mol/h of pyridine and 0.0194 mol/h of β-picoline and 0.0008 mol/h of α-picoline are produced.

Example 2 (Comparative)

0.100 mol/h of acrolein of petrochemical origin (composed of 96% acrolein, 1% acetaldehyde, 0.05% propanal and 3% water), 0.0500 mol/h of acetaldehyde (99.5% pure) and 0.200 mol/h of ammonia are introduced into a vaporizer. The gaseous stream is sent over 16 ml of the same HZSM-5/In catalyst placed in a tube raised to 450° C.

The gaseous stream leaving the reactor is absorbed in water and analyzed by gas chromatography to determine the reaction yields.

0.0403 mol/h of pyridine and 0.0181 mol/h of β-picoline and 0.0007 mol/h of α-picoline are produced.

The invention claimed is:

1. A process for synthesizing biosourced pyridine and picolines, comprising:
   a) subjecting a glycerol charge derived from methanolysis of plant oils or animal fats to a dehydration reaction leading to acrolein according to the reaction $CH_2OH-CHOH-CH_2OH \rightarrow CH_2=CH-CHO+2H_2O$ and then
   b) partially condensing of the effluent derived from a), to separate a stream rich in water and a stream rich in acrolein, and
   c) reacting the acrolein obtained from b) with acetaldehyde, in the presence of ammonia, and in gaseous phase at a pressure between 0.5 and 10 bar to obtain, via a condensation reaction, biosourced pyridine and picolines.

2. The process as claimed in claim 1, wherein a) is performed in a reactor in gas phase at a temperature ranging from 150° C. to 500° C., and a pressure of between 1 and 5 bar in the presence of a solid acid catalyst that is insoluble in the reaction medium, with a Hammett acidity, $H_0$, of less than +2 and chosen from natural or synthetic siliceous materials or acidic zeolites; mineral supports, oxides coated with mono-, di-, tri- or polyacidic inorganic acids, mixed oxides, or heteropolyacids or salts of heteropolyacids.

3. The process as claimed in claim 1, wherein during b), the gaseous effluent obtained from dehydration is subjected to "quench" cooling, in a condensation unit (2) operating at a temperature generally of between 0 and 90° C., separating out at the bottom an aqueous solution comprising heavy compounds, acrylic acid, acetic acid, glycerol polyethers, glycerol acetals and residual glycerol, and at the top a gaseous fraction containing acrolein, propionaldehyde, acetaldehyde and unreacted gases $O_2$ and $N_2$ and also uncondensable gases CO and $CO_2$, the head fraction then being subjected to a purification to obtain a desired quality of acrolein, with or without separation of the acetaldehyde, which may be subjected to the third step.

4. The process as claimed in claim 3, wherein said head fraction is sent to a second absorption column (4), purging at the top of the column uncondensable compounds via line (14) and separating out at the bottom an aqueous acrolein solution also containing the by-products.

5. The process as claimed in claim 4, wherein the aqueous acrolein solution derived from (4) is sent to a distillation column (5) where an acrolein-rich fraction containing acetaldehyde is separated out at the top (87) and an aqueous solution is separated out at the bottom (9) and is recycled into the absorption column (4).

6. The process as claimed in claim 4, wherein the aqueous acrolein solution obtained from (4) is sent to a distillation column (5), where a light fraction enriched in acetaldehyde is separated out at the top (8) and an aqueous acrolein solution is separated out at the bottom and is sent into a second column (6) where a fraction enriched in acrolein is separated out at the top (7) and an aqueous solution is separated out at the bottom (9) and is recycled into the absorption column (4).

7. The process as claimed in claim 4, wherein the aqueous acrolein solution obtained from (4) is sent to a distillation column (5) where a light fraction containing acetaldehyde is separated out at the top (8), and a fraction (7) enriched in acrolein is withdrawn laterally in an intermediate zone, and an aqueous solution is separated out at the bottom (9) and is recycled into the absorption column (4).

8. The process as claimed in claim 1, wherein during c), the acrolein obtained in b) is reacted in a reactor (15) with acetaldehyde in the presence of ammonia to obtain, via a condensation reaction, biosourced pyridine and picolines, this reaction being performed in the gaseous phase at a temperature of between 300 and 600° C., at an hourly space velocity (HSV) of 500 to 5000 $h^{-1}$ and in the presence of a solid acid catalyst consisting of a silica-alumina optionally comprising a promoter.

9. The process as claimed in claim 1, wherein acetaldehyde entering the reaction is partly derived from a) and partly added during c).

10. The process as claimed in claim 1, wherein acetaldehyde added is obtained from bioethanol.

11. The process as claimed in claim 1, wherein acetaldehyde is added to the reaction medium in an amount such that the acrolein/acetaldehyde mole ratio is between 0.8 and 1.2, and ammonia is added in an amount such that the ammonia/acrolein+acetaldehyde mole ratio is between 2 and 20.

12. The process as claimed in claim 6, a portion of acrolein-rich stream is withdrawn at (7'), such that the remaining amount of acrolein stream sent to a reactor (15) where acrolein from b) is reacted with acetaldehyde, such that the acrolein (7)/acetaldehyde (8) mole ratio is between 0.8 and 1.2, this being done while dispensing with additional feed.

13. The process according to claim 2, wherein a) is performed at a temperature of 250-350° C.

14. The process according to claim 8, wherein the solid catalyst has a Si/Al ratio greater than 10.

15. The process according to claim 11, wherein the acrolein/acetaldehyde ratio is 0.9 to 1.1.

* * * * *